United States Patent [19]

Helgerson et al.

[11] Patent Number: 5,695,499
[45] Date of Patent: Dec. 9, 1997

[54] MEDICAL DEVICE SUPPORTED BY SPIRALLY WOUND WIRE

[75] Inventors: Jeffrey A. Helgerson; Wade M. Johnson, both of Minneapolis, Minn.

[73] Assignee: Schneider (USA) Inc., Plymouth, Minn.

[21] Appl. No.: 734,303

[22] Filed: Oct. 21, 1996

Related U.S. Application Data

[63] Continuation of Ser. No. 330,052, Oct. 27, 1994, abandoned.

[51] Int. Cl.$^6$ .................................................. A61F 11/00
[52] U.S. Cl. .................................................. 606/108; 606/198
[58] Field of Search .......................... 606/108, 192, 606/198, 200; 604/164, 264, 280, 282

[56] References Cited

U.S. PATENT DOCUMENTS

| | | | |
|---|---|---|---|
| 3,528,406 | 9/1970 | Jeckel et al. | 606/108 |
| 4,580,568 | 4/1986 | Gianturco . | |
| 4,655,771 | 4/1987 | Wallsten | 623/1 |
| 4,665,918 | 5/1987 | Garza et al. . | |
| 4,681,110 | 7/1987 | Wiktor . | |
| 4,732,152 | 3/1988 | Wallsten et al. . | |
| 4,768,507 | 9/1988 | Fischell et al. | 606/108 |
| 4,848,344 | 7/1989 | Sos et al. . | |
| 4,875,480 | 10/1989 | Imbert . | |
| 5,026,377 | 6/1991 | Burton et al. | 606/108 |
| 5,061,275 | 10/1991 | Wallsten et al. | 623/1 |
| 5,201,757 | 4/1993 | Heyn et al. | 606/198 |
| 5,209,734 | 5/1993 | Hurley et al. | 604/282 |
| 5,279,561 | 1/1994 | Rocher et al. | 604/96 |
| 5,306,249 | 4/1994 | Don Michel | 606/194 |
| 5,372,587 | 12/1994 | Hammerslag et al. | 604/282 |
| 5,439,000 | 8/1995 | Gunderson et al. | 604/282 |
| 5,484,444 | 1/1996 | Braunschweiler et al. | 606/108 |

FOREIGN PATENT DOCUMENTS 9305842  4/1993  WIPO .

*Primary Examiner*—Glenn K. Dawson
*Attorney, Agent, or Firm*—Peter C. Richardson; Lawrence C. Akers; Philip C. Strassburger

[57] ABSTRACT

A stent delivery device is disclosed that includes an inner tube having a distal portion which carries the stent on the delivery device. At least part of the inner tube is formed from a spirally wound wire. A movable outer tube is used to constrain the stent in a radially contracted state on the distal portion of the inner tube. A substantially straight elongate wire is configured inside the spirally wound wire and bonded at the distal and proximal portions of the wound wire. The outer tube may have at least one side port adjacent to the distal portion in communication with the annular space between the outer tube and the inner tube allowing radiopaque fluid to be injected through the annular space and out the side port in the vicinity of the stent.

24 Claims, 3 Drawing Sheets

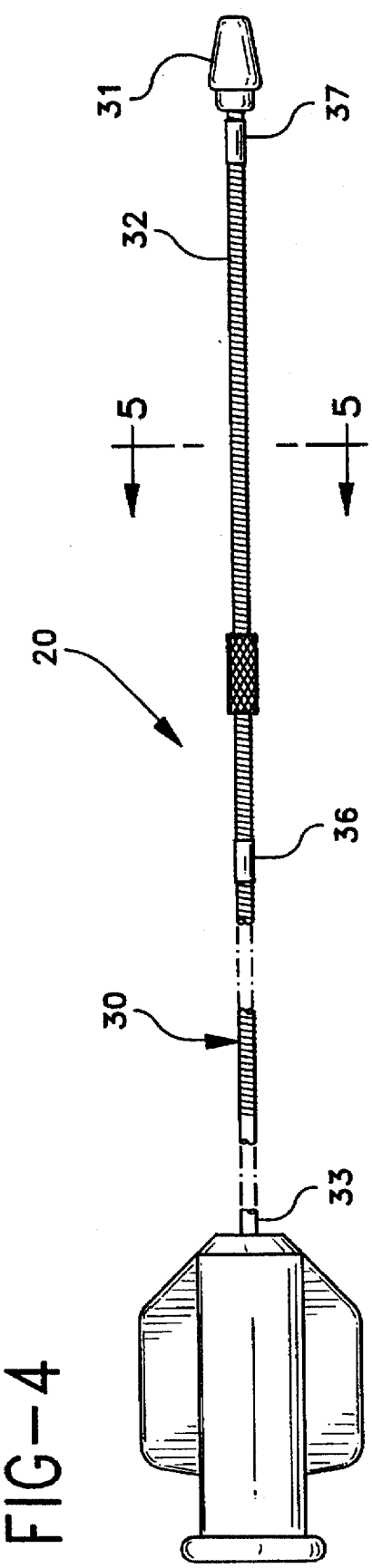
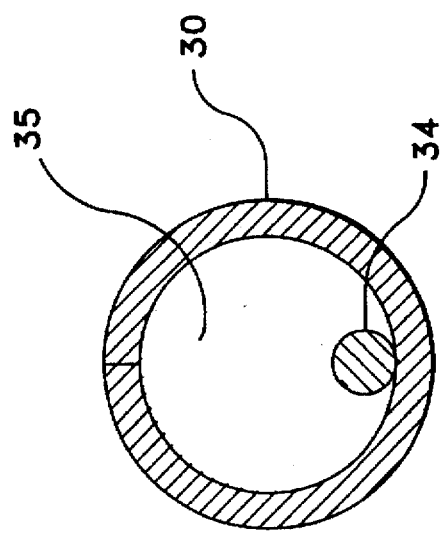
FIG-4
FIG-5

MEDICAL DEVICE SUPPORTED BY SPIRALLY WOUND WIRE

This is a continuation of application Ser. No. 08/330,052, filed on Oct. 27, 1994, now abandoned.

BACKGROUND OF THE INVENTION

In recent years, stents have been developed for use in various body lumens to maintain the patency of such lumens. Applications for stents include biliary ducts, the esophagus, respiratory tracts, and various blood vessels. In order to deliver a stent to a treatment site within the body, the stent should be radially expandable from a small diameter configuration for transport to a treatment site. Once at the treatment site, the stent should be radially expandable to attain a larger diameter configuration to engage the walls defining the body lumen to be treated.

Radially self-expanding stents, such as described in U.S. Pat. Nos. 4,655,771 and 5,061,275 are generally preferred because of their self-expanding characteristics. There is no need for a device to radially expand these stents once the stent is at the treatment site. Instead, the stent can be delivered to the treatment site in a reduced diameter configuration and then the stent can be allowed to radially self-expand into engagement with the wall defining the body lumen to be treated.

Delivery devices known in the art generally have a movable outer tubular member that constrains the stent in a contracted state on an inner catheter. The outer tubular member is removed from contact with the stent to allow the stent to radially self-expand for deployment in a body lumen.

Where the stent is to be delivered to a remote body site, such as the biliary duct or a blood vessel, the stent delivery device will preferably afford the physician with the ability to visualize the placement of the stent under fluoroscopy. A desirable characteristic of a stent device is the ability to inject radiopaque or contrast media through the device and illuminate the area of treatment. With this ability the physician can ensure that the stent is deployed at the treatment site. Currently available stent delivery devices are deficient in this regard because they do not have the ability to allow radiopaque or contrast fluid to be injected directly to the area where visualization is most important for the physician.

Another desirable characteristic for a stent delivery device is the ability to "recapture" a partially deployed stent. This feature would allow a physician to reposition a stent after partial deployment if the location at partial deployment is not correct.

The stent delivery device should also be both flexible and longitudinally rigid. Flexibility is desirable in order for the stent delivery device to navigate the sometimes tortuous path used to get to the treatment site. This is especially true where the treatment site is a blood vessel, such as the renal, carotid or coronary arteries. Longitudinal rigidity is preferred to provide "pushability". This "pushability" ensures that the physician will be able to push the stent delivery device through the anatomy to the appropriate treatment site.

Therefore, it would be desirable to provide a stent delivery device that affords the physician with the ability to observe the stent during deployment under fluoroscopy.

It would also be desirable to provide a stent delivery device that has the ability to "recapture" a partially deployed stent.

It would be further desirable to provide a stent delivery device that is flexible.

It would be still further desirable to provide a stent delivery device that is longitudinally rigid.

SUMMARY OF THE INVENTION

These and other objects are achieved by the stent delivery device of the present invention. The stent delivery device includes an elongate inner tube which may or may not include a central lumen for accommodating a guidewire. At least a portion of the inner tube is formed from a coil wire. The proximal portion of the inner tube may be formed from a stiff, preferably metallic, tube. The distal portion of the inner tube may be covered with a suitable polymer if desired.

A flexible outer hose may surround the inner tube to confine the stent in a radially contracted state on the inner tube. When it is desired to deploy the stent at a treatment site, the outer hose is moved proximally with respect to the inner tube to uncover the stent and allow the stent to radially self-expand into engagement with the vessel wall. One or more side ports may be formed in the flexible outer hose near its distal end. This allows radiopaque fluid to be injected through the annular space between the flexible outer hose and the inner tube and exit from the side ports adjacent to the stent during deployment. As a result, the physician has the opportunity to observe the stent during deployment and ensure that the stent is properly positioned.

A small recapture sleeve may be located on the inner tube in the area that carries the stent. This recapture sleeve may have a soft durometer and a plurality of grooves formed therein. This combination of features creates high friction and mechanical interference between the recapture sleeve and the stent to hold the stent on the inner tube as the outer tube moves proximally and distally over most of the length of the stent. This provides the delivery device with the "recapturability" characteristic.

In sum, the present invention relates to a device for delivering a radially self-expanding stent to a remote treatment site in a body passage, having an elongate inner tube with a distal portion and a proximal portion made of a spirally wound wire; an outer tube movably surrounding at least part of the inner tube; and a substantially straight elongate wire configured inside or outside the spirally wound wire and bonded to the spirally wound wire at the distal portion and at the proximal portion of the spirally wound wire. The device may be laterally flexible but essentially longitudinally rigid. The straight wire may have a generally circular cross-section with a diameter of about 0.005 inches (0.127 mm) to about 0.01 inches (0.254 mm), and the straight wire may have a generally rectangular cross-section and sides of from about 0.002 inches (0.051 mm) to about 0.012 inches (0.305 mm). The spirally wound wire may have a generally rectangular cross-section and sides of from about 0.002 inches (0.051 mm) to about 0.016 inches (0.406 mm). The spirally wound wire may have a generally circular cross-section with a diameter of about 0.004 inches (0.102 mm) to about 0.02 inches (0.51 mm). The straight wire and/or the spirally wound wire may be made of a material such as stainless steel, a superelastic alloy such as nitinol, nickel and its alloys, or titanium and its alloys.

The present invention also relates to a device for delivering a radially self-expanding stent to a remote treatment site in a body passage, having: an elongate inner tube with a distal portion and a proximal portion made of a spirally wound wire; an outer tube having a distal portion and a proximal portion movably surrounding at least the distal portion of the inner tube wherein the outer tube has at least one side port located in the distal portion of the outer tube; and a substantially straight elongate wire configured inside or outside the spirally wound wire and bonded to the spirally wound wire at the distal portion and at the proximal portion of the spirally wound wire.

The present invention also relates to a device for delivering a radially self-expanding stent to a remote treatment site in a body passage, having an elongate inner tube with a distal portion and a proximal portion made of a spirally wound wire; an outer tube movably surrounding at least part of the inner tube; a substantially straight elongate wire configured inside or outside the spirally wound wire and bonded to the spirally wound wire at the distal portion and at the proximal portion of the spirally wound wire; and a recapture sleeve coaxially located along the distal portion of the elongate inner tube. The recapture sleeve may be made of a tube having a soft durometer and it may have a plurality of grooves formed therein. The elongate inner tube may be at least partially coated by a lubricious material on the inside, on the outside, or on both the inside and outside.

The present invention also relates to a method of deploying a radially self-expanding stent in a remote treatment site in a body passage, including the steps of inserting a delivery device having an elongate inner tube having a distal portion and a proximal portion made of a spirally wound wire, an outer tube having a distal portion and a proximal portion movably surrounding at least part of the inner tube wherein the outer tube has at least one side port located in the distal portion of the outer tube, and a substantially straight elongate wire configured inside or outside the spirally wound wire and bonded to the spirally wound wire at the distal portion and at the proximal portion of the spirally wound wire; partially deploying the stent by moving the outer tube in a proximal direction; and injecting radiopaque fluid through an annular space between the inner tube and the outer tube so the radiopaque fluid flows through the at least one side port in the area where the stent is to be deployed.

BRIEF DESCRIPTION OF THE DRAWINGS

The above and other objects and advantages of this invention will be apparent upon consideration of the following detailed description, taken in conjunction with the accompanying drawings, in which like reference characters refer to like parts throughout. The following detailed description and drawings are provided in order to illustrate, and not limit, the present invention.

FIG. 4 is a side view of an inner tube of the present invention;

FIG. 5 is a view taken along line 5—5 of FIG. 4; and

DETAILED DESCRIPTION OF THE INVENTION

Figure 1:
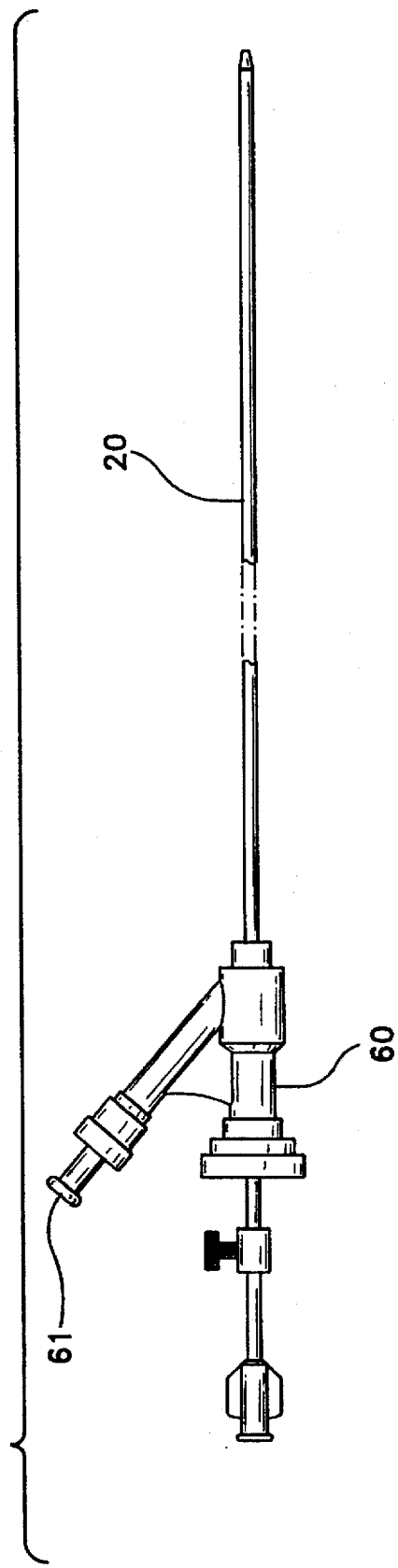
FIG. 1 is a side view, partially in section of a first embodiment of the present invention.
Figure 3:
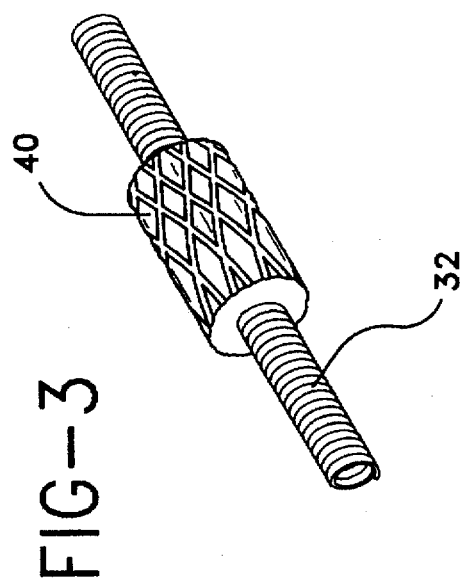
FIG. 3 is a perspective view of a recapture sleeve of the present invention.
Figure 2:
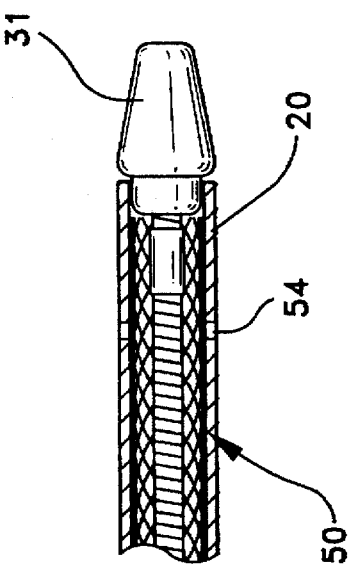
FIG. 2 is an enlarged side view of the distal portion of a second embodiment of the present invention.
Figure 6:
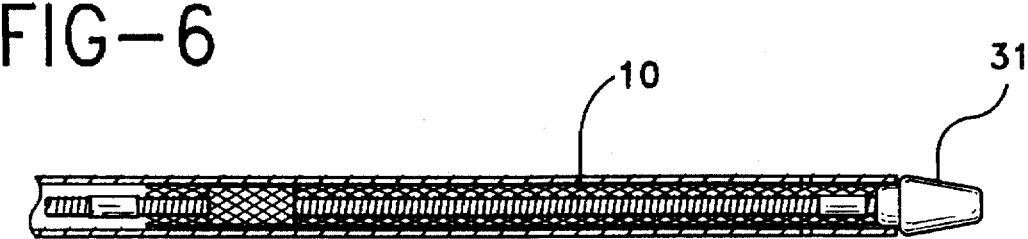
FIGS. 6–8 are side views of a distal portion of a stent delivery device of the present invention and a radially self-expanding stent in various stages of a stent deployment operation.
Figure 7:
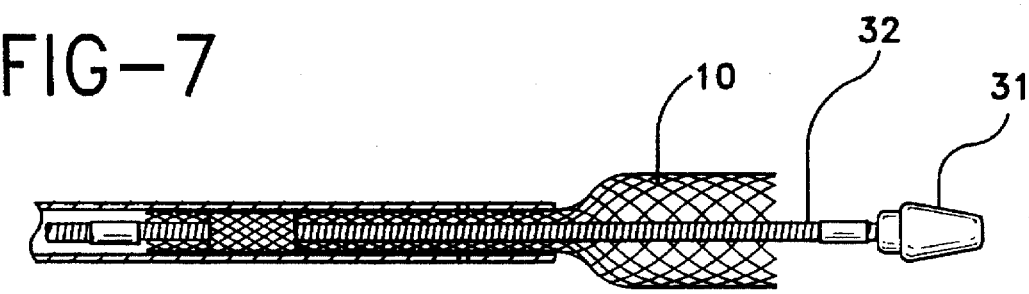
Figure 8:
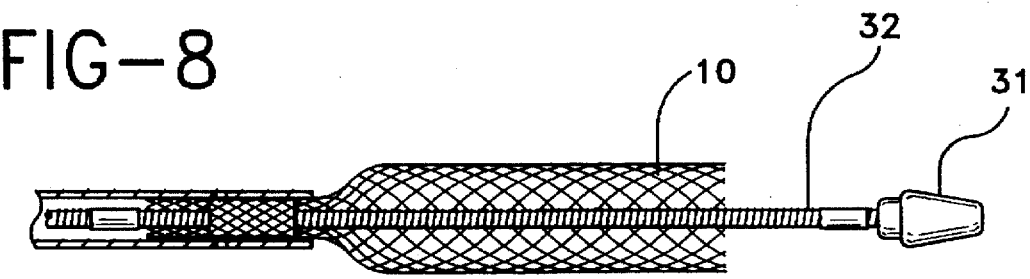

The following detailed description of the delivery device 20 is based on its use with a self-expanding stent 10 as described in U.S. Pat. Nos. 4,655,771 and 5,061,275. Such a stent 10 has a generally wire braided mesh structure. However, it is to be understood that delivery device 20 could be used with other radially self-expanding stents.

Stent 10 is placed on a stent delivery device 20 in a radially contracted state for delivery to the treatment site in a body vessel. Stent 10 is carried by the distal portion of delivery device 20. The proximal portion of delivery device 20 generally remains outside of the body for manipulation by the operator.

Delivery device 20 comprises an elongate inner tube 30, preferably having an axially extending lumen 35 therethrough. Inner tube 30 has a distal portion 32 that is formed from a coiled wire. This wire forming distal portion 32 may be wound over a mandrel with a suitable outer diameter in such a manner that the resulting coils are closely spaced similar to a solid spring. The wire forming distal portion 32 can have either a round or rectangular cross section. A rectangular cross section is preferred for a number of reasons. It presents a smoother inner surface to lumen 35 so that a guidewire can be easily slid through, if desired. It also minimizes the wall thickness of inner tube 30. The dimensions of the wire may be chosen to maximize the strength and flexibility of distal portion 32 while minimizing its size. A wire having dimensions of 0.004 inches by 0.012 inches (0.102 mm by 0.305 mm) is preferred, although other dimensions may be utilized depending upon the particular application. For instance, the spirally wound wire may have a generally rectangular cross-section with dimensions of about 0.002 inches (0.051 mm) to about 0.016 inches (0.406 mm). This wire can be formed of any suitable material such as stainless steel, a superelastic alloy such as nitinol, nickel and its alloys or titanium and its alloys. Preferably stainless steel is used.

The spirally wound wire will generally be tightly wound, and in some cases wound coils will firmly abut each other. In some cases the wound wire will be wound such that spaces exist between some or all of the coils.

A straight wire 34 extends through lumen 35 along a length of distal portion 32 and is bonded thereto at each end. In other embodiments, straight wire 34 will be configured outside of inner tube 30. In some cases, more than one wire 34 will preferably be configured inside and/or outside the spirally wound wire. Wire 34 prevents inner tube 30 from unraveling inside the body like a spring, and allows the wound wire to remain essentially longitudinally rigid. Wire 34 can be bonded to inner tube 30 by any standard means such as arc welding, soldering, brazing or using adhesives. However, laser welding is preferred. It can be bonded at one or more points at each end. It will generally be bonded at or near the ends of the wound wire, but bonding may alternatively be performed away from the ends of the wound wire. Wire 34 preferably has a circular cross-section with a diameter of 0.0065 inches. Generally, diameters of about 0.005 inches (0.127 mm) to 0.01 inches (0.254 mm) are suitable. Smaller diameters will generally minimize binding with a guide wire that may be passed through lumen 35. Other dimensions may be utilized depending upon the particular application. Wire 34 could also have a rectangular cross section, and may have sides from about 0.002 inches (0.051 mm) to about 0.012 inches (0.305 mm). A suitable polymer such as polyurethane, FEP, PTFE or silicone may be used to cover the outer diameter of distal portion 32. Such a covering can increase the structural strength, and can also confine wire 34 when it is configured outside of inner tube 30. The covering can also increase the lubriciousness of distal portion 32. However, it has been found that an uncovered distal portion 32 is generally sufficiently lubricious and that there is minimal interference with outer tube 50.

The elongate inner tube of the present invention will typically be from about 50 to about 250 cm, depending upon the particular indication. The portion made of spirally wound wire may be the entire length of the inner tube or less than the entire length. In the case of renal indications, for instance, the proximal most 7–15 inches (18–38 cm) of the inner tube may comprise a tube of rigid material, and the remainder may comprise a spirally wound wire. In some cases, the spirally wound wire will extend to the proximal most section of the elongate inner tube and be configured inside of a tube of rigid material in the proximal portion.

One or more standard radiopaque markers 36, 37 can be placed along the distal portion 32 such that they are located on one side or on either side of stent 10 when it is placed on distal portion 32.

At its distal end, inner tube 30 is provided with a tip 31, through which lumen 35 continues. Tip 31 is preferably tapered to facilitate the insertion of delivery device 20 through a narrow opening in a body vessel. It is generally soft with no sharp edges. Tip 31 is generally flexible so it is easily trackable over a guide wire. Preferably a UV curable adhesive is used to bond tip 31 to the wound wire that forms distal portion 32. In addition, tip 31 may be plasma etched to provide a clean surface for better adhesion between the coiled wire and tip 31.

The proximal portion 33 of inner tube 30 may be formed from a tube of rigid material, such as stainless steel, composite, polymer, or some other suitably rigid material. Proximal portion 33, when formed from a rigid material, provides added "pushability" to delivery device 20 and also provides a "working surface" for the deployment mechanism of delivery device 20. Preferably an adhesive such as cyanoacrylate is used to bond the distal end of proximal portion 33 to the proximal end of distal portion 32.

Preferably a short, low durometer recapture sleeve 40 is coaxially located about distal portion 32. The length of recapture sleeve 40 must be sufficient to hold stent 10 in place. It has been found that recapture sleeve 40 is preferably 2–3 mm in length. Generally, lengths of 1 mm to the length of the constrained stent on the delivery device are suitable. Recapture sleeve 40 is preferably formed from a silicone or other polymeric tubing such as polyurethane with a Shore hardness between about 30A and 90A. Such a low durometer for recapture sleeve 40 creates a higher frictional force with stent 10 than exists between outer tube 50 and stent 10. Recapture sleeve 40 is preferably formed with a plurality of grooves formed therein. These grooves result in a mechanical interference fit between stent 10 and recapture sleeve 40 to aid in holding stent 10 on inner tube 30. Thus when stent 10 has been partially deployed by proximal movement of outer tube 50 and it is desired to recapture stent 10 to reposition stent 10 in the body lumen, outer tube 50 can be moved distally over stent 10 to reconstrain stent 10 on inner tube 30 without stent 10 moving axially along inner tube 30 with outer tube 50. The exact location of recapture sleeve 40 on inner tube 30 depends on the desired maximum amount that stent 10 can be deployed with recapturability still feasible. Preferably recapture sleeve 40 should be located along the most proximal quarter of the length of stent 10 when it is constrained on inner tube 30, such as about 3–10 mm distal from the proximal marker band 36.

Outer tube 50 surrounds inner tube 30 in coaxial fashion. Preferably outer tube 50 is formed from any suitable polymer such as polyurethane, polyether block amide nylon or some other polyamide. Outer tube 50 may be coated on the inside and/or on the outside with a lubricious coating, such as silicone, to facilitate ease of movement in the vessel and during deployment or during recapturing of stent 10. The proximal end of outer tube 50 is connected to a valve body 60 having a side port 61. This arrangement allows outer tube 50 to be moved off of stent 10 by moving valve body 60 in the proximal direction. Side port 61 allows fluid such as radiopaque fluid to be injected between outer tube 50 and inner tube 30. Valve body 60 preferably extends over proximal portion 33 of inner tube 30. This allows valve body 60 to be slid easily over inner tube 30 and locked to inner tube 30 by means of compression gasket and threaded screw knob.

Outer tube 50 may include at least one and preferably two side ports 54 located along its distal portion. Additional side ports 54 could also be employed. Side ports 54 allow radiopaque fluid that is injected through the annular space between outer tube 50 and inner tube 30 to exit delivery device 20 in the region where stent 10 is deployed. Side ports 54 are preferably located circumferentially about outer tube 50 such that each one is offset from the other by 180°. The use of multiple ports 54 allows flow of radiopaque fluid from delivery device 20 even if one port is blocked. Side ports 54 should have a large enough diameter to allow sufficient radiopaque fluid flow therefrom to "illuminate" the area to be treated. It has been found that a diameter of about 0.010–0.025 inches (0.254–0.635 mm), and preferably about 0.015 inches (0.381 mm) is suitable where delivery device 20 is used to deploy a stent in the renal artery of a human. As a result, the physician using delivery device 20 to deploy stent 10 can visualize stent 10 under fluoroscopy during the stent deployment procedure because the radiopaque fluid will "illuminate" the vessel where the stent is to be deployed. The physician can thus ensure that stent 10 is properly located at the treatment site prior to complete deployment of stent 10.

The location of side ports 54 will preferably be proximal of the distal end of outer tube 50. Without side ports 54, the radiopaque fluid would generally exit outer tube 50 at its distal end and would flow past the stent deployment area because of the flow of body fluid past delivery device 20. Having side ports 54 proximal of the distal end of outer tube 50 allows the radiopaque fluid to flow out of delivery device 20 in the exact area of stent deployment. A suitable location for side ports 54 is about 4–10 mm proximal to the distal end of outer tube 50, and preferably about 7 mm proximal to the distal end of the outer tube 50. Side ports 54 should not interfere with the distal and proximal ends of stent 10 during deployment or recapture. Where stent 10 is formed of a braided wire structure, the ends of stent 10 contain a plurality of exposed wire ends. If side ports 54 were to cross over either end of the distal end of stent 10, it is possible that one of the exposed wires would engage with one of side ports 54 and prevent deployment or recapture. Thus side ports 54 should be located on outer tube 50 such that side ports 54 are proximal of the distal end of stent 10 when stent 10 is constrained on inner tube 30 by outer tube 50 and distal of the proximal end of stent 10 when it is partially deployed on inner tube 30 by outer tube 50.

To deliver stent 10 to a treatment site in a body vessel, stent 10 is placed in a radially compressed state in a coaxial relationship over distal portion 33. Stent 10 is constrained on inner tube 30 by outer tube 50. It is important that stent 10 not be confined too tightly on inner tube 30. Outer tube 50 should apply just enough force to stent 10 to hold stent 10 in place. Outer tube 50 can be removed from surrounding relation to stent 10 by pulling valve body 60 and outer tube 50 in a proximal direction. Along with the movement of outer tube 50 in the proximal direction, the distal end of stent 10 will be exposed in a radial direction to engagement against the wall of the body vessel. At this point, radiopaque fluid can be injected in the annular space between outer tube 50 and inner tube 30 so that it exits through side ports 54. This allows the physician to view the location of stent 10 under fluoroscopy. If the physician observes that stent 10 is properly placed, outer tube 50 can be moved further proximally to deploy more of stent 10 until stent 10 is completely deployed. On the other hand, if stent 10 is improperly located, outer tube 50 can be moved distally and/or inner tube 30 can be moved proximally to recapture stent 10 back onto inner tube 30 and under outer tube 50 for movement to the proper location.

A safety stop can be positioned along proximal portion 33 of inner tube 30 proximal of valve body 60. The safety stop is comprised of a locking tubular member that prevents movement of valve body 60 in the proximal direction when safety stop is locked in place. Thus safety stop can be located so that it prevents valve body 60 from moving too far proximally to prevent complete deployment of stent 10. In this way, the operator of delivery device 20 is reminded to check the location of stent 10 prior to complete deployment.

Another feature of the invention is the use of etched markings on proximal portion 33. These markings are located such that they give the operator of delivery device 20 an indication of the amount that stent 10 has been deployed when valve body 60 reaches the markings.

Thus it is seen that a stent delivery device is provided that provides the physician with the opportunity to view the location of the stent during the deployment procedure, that allows for "recapturing" the stent and that is flexible and longitudinally rigid. The described embodiments are presented for purposes of illustration and are not limiting.

What is claimed is:

1. A medical device for transluminal placement in a remote treatment site in a body passage, comprising:

an elongate inner tube comprising a spirally wound wire having an open distal end and a proximal end, the inner tube forming a lumen adapted to receive a guidewire therethrough;

an outer tube surrounding at least part of the inner tube; and a substantially straight elongate wire adjacent and bonded to the spirally wound wire at or near the distal end and at or near the proximal end thereof.

2. The device of claim 1 wherein the substantially straight elongate wire is configured inside the spirally wound wire and the device is laterally flexible but essentially longitudinally rigid.

3. The device of claim 1 wherein the straight wire has a generally circular cross-section with a diameter of about 0.005 inches (0.127 mm) to about 0.01 inches (0.254 mm).

4. The device of claim 1 wherein the straight wire has a generally rectangular cross-section and has sides of from about 0.002 inches (0.051 mm) to about 0.012 inches (0.305 mm).

5. The device of claim 1 wherein the spirally wound wire has a generally rectangular cross-section and has sides of from about 0.002 inches (0.051 mm) to about 0.016 inches (0.406 mm).

6. The device of claim 1 wherein the spirally wound wire has a generally circular cross-section with a diameter of about 0.004 inches (0.102 mm) to about 0.02 inches (0.51 mm).

7. The device of claim 1 wherein at least one of the straight wire and the spirally wound wire is formed from a material selected from the group consisting of stainless steel, a superelastic alloy, nitinol, nickel and its alloys and titanium and its alloys.

8. The device of claim 1, further comprising a self-expanding stent constrained on the inner tube by the outer tube.

9. The medical device of claim 1 wherein the outer tube is adapted for longitudinal movement relative to the inner tube.

10. The medical device of claim 1 further comprising a guidewire disposed within the lumen.

11. A medical device for transluminal placement in a remote treatment site in a body passage, comprising:

an elongate inner tube having a distal portion and a proximal portion comprising a spirally wound wire having a distal end and an open proximal end, the inner tube forming a lumen adapted to receive a guidewire therethrough;

an outer tube having a distal portion and a proximal portion surrounding at least the distal portion of the inner tube wherein the outer tube has at least one side port located in the distal portion of the outer tube; and a substantially straight elongate wire adjacent and bonded to the spirally wound wire at or near the distal end and at or near the proximal end thereof.

12. The device of claim 11 wherein the substantially straight elongate wire is configured inside the spirally wound wire and the device is laterally flexible but essentially longitudinally rigid.

13. The device of claim 11, further comprising a self-expanding stent constrained on the inner tube by the outer tube.

14. The medical device of claim 11 wherein the outer tube is adapted for longitudinal movement relative to the inner tube.

15. The medical device of claim 11 further comprising a guidewire disposed within the lumen.

16. A device for delivering a radially self-expanding stent to a remote treatment site in a body passage, comprising:

an elongate inner tube comprising a spirally wound wire having an open distal end, a proximal end, and a distal portion, the inner tube forming a lumen adapted to receive a guidewire therethrough;

an outer tube movably surrounding at least part of the inner tube;

a substantially straight elongate wire adjacent and bonded to the spirally wound wire at or near the distal end and at or near the proximal end thereof; and a recapture sleeve coaxially located along the distal end of the elongate inner tube.

17. The device of claim 16 wherein the recapture sleeve is formed from a tube having a soft durometer and has a plurality of grooves formed therein.

18. The device of claim 16 wherein the elongate inner tube has an inside and an outside and the inner tube is at least partially coated by a lubricious material on least one of the inside and outside.

19. The device of claim 16 wherein the substantially straight elongate wire is configured inside the sprially wound wire and the device is laterally flexible but essentially longitudinally rigid.

20. The device of claim 16, further comprising a self-expanding stent constrained on the tuner tube by the outer tube.

21. The medical device of claim 16 further comprising a guidewire disposed within the lumen.

22. A method of deploying a radially self-expanding stent in a remote treatment site in a body passage, comprising:

inserting a delivery device into a body lumen, the device having an elongate inner tube comprising a spirally wound wire having a distal end and a proximal end, the inner tube forming a lumen adapted to receive a guidewire, an outer tube having a distal portion and a proximal portion movably surrounding at least part of the inner tube wherein the outer tube has at least one side port located in the distal portion of the outer tube, a substantially straight elongate wire adjacent and bonded to the spirally wound wire at or near the distal end and at or near the proximal end of the sprially wound wire, and self-expanding stent constrained on the inner tube by the outer tube;

partially deploying the stent by moving the outer tube in a proximal direction; and injecting radiopaque fluid through an annular space between the inner tube and the outer tube so the radiopaque fluid flows through the at least one side port in the area where the stent is to be deployed.

23. The method of claim 22 wherein the substantially straight elongate wire is configured inside the spirally wound wire and the device is laterally flexible but essentially longitudinally rigid.

24. The method of claim 22 wherein a guide is disposed within the lumen.

* * * * *